United States Patent [19]

Nardella

[11] Patent Number: 5,201,900
[45] Date of Patent: Apr. 13, 1993

[54] BIPOLAR SURGICAL CLIP

[75] Inventor: Paul C. Nardella, North Easton, Mass.

[73] Assignee: Medical Scientific, Inc., Taunton, Mass.

[21] Appl. No.: 842,899

[22] Filed: Feb. 27, 1992

[51] Int. Cl.⁵ ............................................. A61B 17/00
[52] U.S. Cl. ..................................... 606/157; 606/28; 606/151; 606/158; 227/902
[58] Field of Search ............... 606/151, 157, 158, 221, 606/50, 51, 47; 128/785; 127/902; 174/159

[56] References Cited

U.S. PATENT DOCUMENTS

| | | | |
|---|---|---|---|
| 339,769 | 4/1886 | Hayes | 174/159 |
| 1,705,144 | 3/1929 | Tobey | 174/159 |
| 3,357,296 | 12/1967 | Lefever | 174/159 |
| 3,766,926 | 10/1973 | Bliss | 606/151 |
| 4,137,919 | 2/1979 | Farin et al. | 606/51 |
| 4,476,865 | 11/1984 | Failla et al. | |
| 4,586,503 | 5/1986 | Kirsch et al. | |
| 4,590,937 | 5/1986 | Deniega | |
| 4,651,737 | 3/1987 | Deniega | |
| 4,686,980 | 8/1987 | Williams et al. | 606/50 X |
| 4,748,982 | 6/1988 | Horzewski et al. | 606/192 |
| 4,799,481 | 1/1989 | Transue et al. | |
| 4,815,466 | 3/1989 | Perlin | |
| 4,826,945 | 5/1989 | Cohn et al. | |
| 4,834,096 | 5/1989 | Oh et al. | |
| 4,844,066 | 7/1989 | Stein | |
| 4,890,610 | 1/1990 | Kirwan, Sr. et al. | 606/51 |
| 5,052,386 | 10/1991 | Fischer | 128/207.15 |

Primary Examiner—Stephen C. Pellegrino
Assistant Examiner—Jeffrey A. Schmidt
Attorney, Agent, or Firm—Lahive & Cockfield

[57] ABSTRACT

A bipolar electrosurgical clip is provided having two opposed prong members which are connected by a bridge member. The surface of the prong members are preferably coated with a conductive material while the bridge member is made of a highly resistive material which serves to electrically isolate the prong members from each other. One conductive prong member is adapted to serve as an active electrode through which electrosurgical energy is delivered to tissue while deploying the clip. The other conductive prong member serves as a return electrode, communicating through a conductor wire with an electrosurgical generator.

11 Claims, 2 Drawing Sheets

BIPOLAR SURGICAL CLIP

BACKGROUND OF THE INVENTION

This invention relates to surgical clips able to be deployed to tissue through electrosurgical techniques. More importantly, the invention relates to bipolar surgical clips.

Ligation or occlusion of ducts, veins, arteries or blood vessels is common in many surgical procedures. Often it is desirable to do so using one or more surgical clips which are intended to remain in place on either a temporary or a permanent basis. Many of the known surgical clips typically are made entirely of a single type of material such as surgical grade metal (e.g., titanium or stainless steel) or biocompatible polymers.

Some medical procedures require that surgical clips be deployed to permanently ligate a duct, vein, artery or vessel. In such situations it is important that the clip not become dislodged or displaced over time. However, it is believed that approximately 30% of surgical clips intended to be permanently installed become dislodged or displaced over the course of time. Such dislodgement or displacement of the clip can result in the undesirable release of fluid or blood.

Although surgical clips generally are administered mechanically, they may also be administered electrosurgically. U.S. patent application Ser. No. 786,574, filed Nov. 1, 1991 and incorporated herein by reference, discloses a surgical clip applicating device in which electrosurgical current is delivered to the clip through an active electrode, and to the adjacent tissue as the clip is deployed. This enables the clip and the adjacent tissue to be fused together, resulting in more secure surgical clips. The electrosurgical clip applicating device is used with a remote ground electrode which is secured to the patient's body, generally at a location remote from the area in which the clip is deployed. Although quite effective for deploying clips, there is some potential for harm to the patient due to the relatively long path through the body over which current must travel to reach the ground electrode.

Accordingly, there is a need for electrosurgical clips which can be safely and effectively deployed through electrosurgical techniques without the use of a remote ground electrode.

It is thus an object of the invention to provide a surgical clip able to be electrosurgically deployed without the use of a remote ground electrode. Another object is to provide a method and apparatus for electrosurgically deploying surgical clips while reducing the length of the current path within the body. Another object is to provide a surgical clip able to be used a bipolar electrosurgical device. Other objects will be apparent from the description which follows.

SUMMARY OF THE INVENTION

The invention relates to a surgical clip construction which enables the clip to be used as a bipolar electrosurgical device. The clip comprises a pair of opposed prong members which each have a contiguous conductive surface over at least part of their outer periphery. A bridge member constructed of a highly resistive material joins the two prong members and serves to electrically isolate the prong members from each other. The clip is bipolar in that one of the prongs may communicate with an active electrode through which current may be delivered to adjacent tissue while the other prong serves as a ground electrode. Electrosurgical application of such a clip results in fusing of the clip to the adjacent tissue and also minimizes any potential risk to the patient which may result from current traveling through the body over relatively long distance from the active electrode to a remote ground electrode.

In another aspect, the surgical clip is made of a highly resistive material, such as a polymer, and the prongs of the clip are coated with a conductive material. The coating of the prongs is sufficient to conduct electricity, but also enables heat to be transferred through the coating and to the underlying polymer substrate and bridge. This enables the clip to become pliant and easily deformed upon deployment. Upon cooling, the clip assumes its rigidity in the configuration in which it was deployed, thus rendering dislodgement less likely.

DETAILED DESCRIPTION OF THE INVENTION

Figure 1:
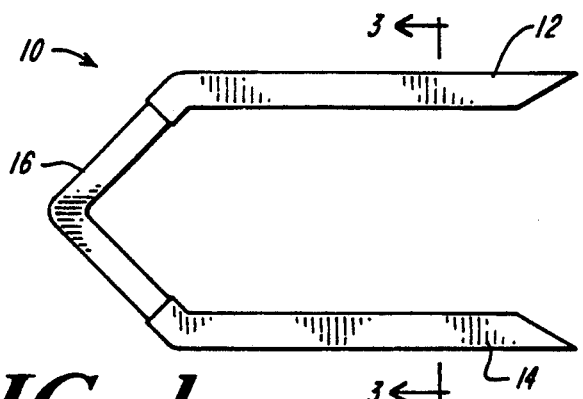
FIG. 1 is a schematic view of a surgical clip according to the present invention.
Figure 2:
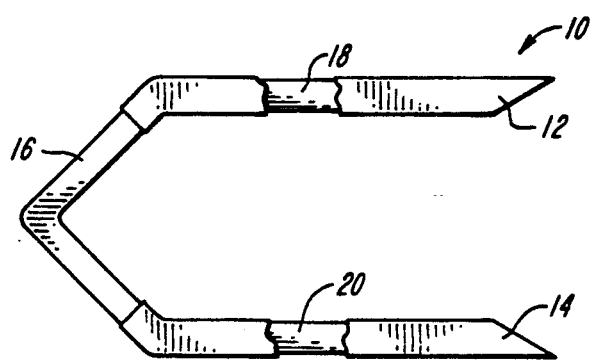
FIG. 2 illustrates the surgical clip of FIG. 1, showing a partially cutaway view of each of the prong members.
Figure 3:
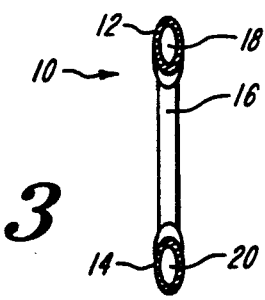
FIG. 3 is a sectional view of the clip of FIG. 1 along lines 3—3.

FIGS. 1 through 3 illustrate the basic construction of a bipolar surgical clip constructed according to the present invention. As illustrated, the surgical clip 10 comprises opposed prong members 12, 14 which are joined by a bridge member 16. Each of prongs 12, 14 is coated with a material having sufficient conductivity to conduct electrical current. The bridge portion 16 electrically isolates prongs 12, 14 as it is constructed from a highly resistive material with a conductivity insufficient to serve as a conductor of electrical current.

Figure 4:
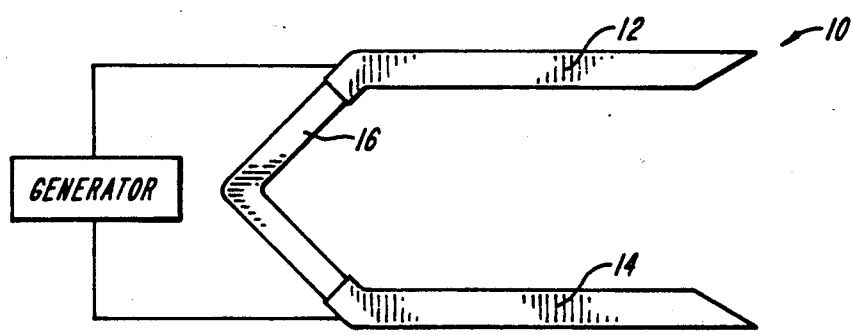
FIG. 4 schematically illustrates the connection of the surgical clips to a source of electrosurgical energy.

As illustrated in FIG. 4, the surgical clip 10 can be connected (through a clip applicating device, not shown) to a source of electrosurgical current such as electrosurgical generator 22. Conductive electrode wire 24 communicates with prong 12, enabling prong 12 to deliver current to adjacent tissue. Prong 14 then serves as the ground or return electrode which communicates with generator 22 through electrical conduit or return electrode wire 26.

A surgical clip may be deployed to tissue by a suitable electrosurgical clip applicating device. An example of one electrosurgical clip applicating device, which requires only minor modification for use of the present clip, is disclosed in U.S. patent application Ser. No. 786,574, filed Nov. 1, 1991.

Figure 5:
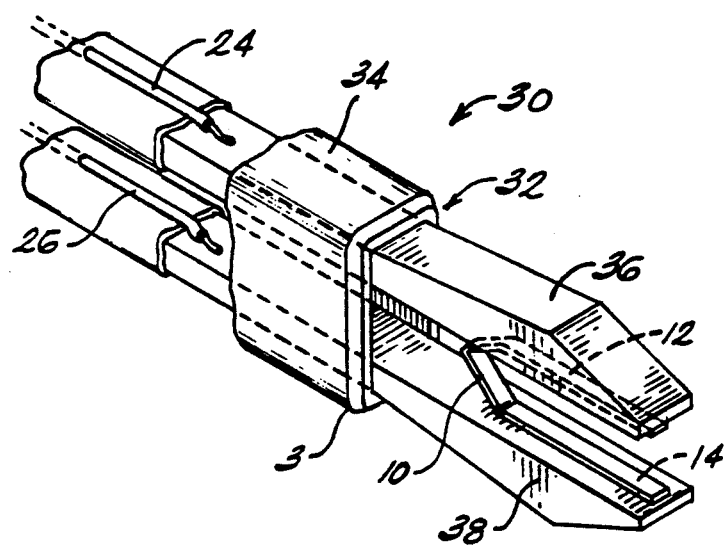
FIG. 5 schematically illustrates a forward portion of an electrosurgical clip application device useful for deploying the surgical clip of FIG. 1.

FIG. 5 illustrates one embodiment of an electrosurgical clip applicating device useful in deploying the bipolar surgical clips of the present invention. The clip applicating device 30, includes the illustrated forward portion 32 having housing 34 and clamping jaw elements 36 and 38. Clamping jaws 36 and 38 are constructed so that they are able to hold clip 10 and, when actuated, close together and deploy the clip. Preferably, one clamping element, such as clamping jaw 36 communicates with a conductor wire 24 which delivers electrosurgical energy to jaw 36 and to prong 12 of clip 10. Clamping jaw 38 is constructed such that it is electrically isolated from jaw 36 and serves as a return electrode which, through wire 26, communicates with a generator (not shown).

Electrical isolation of clamping jaws 36, 38 may be accomplished by constructing the jaws of a highly resistive material and coating a forward, clip contacting portion of the jaws with a conductive material. Conductor wire 24, which delivers electrosurgical current to jaw 36, will contact a conductive portion of the jaw. Similarly wire 26 communicates with a conductive portion of jaw 38 which serves as a return electrode.

Referring to FIGS. 2 and 3, clip 10 may be constructed of a substrate material 18 which is highly resistive and unable to conduct electrical current. A conductive coating material 20 is coated upon the substrate of prong members 12, 14. The conductive coating material 20 is coated at a thickness sufficient to enable the coated portion of the prong to conduct electricity. Preferably, the conductive material is coated in a continuous manner upon prongs 12, 14, leaving a sufficient portion of the bridge member 16 uncoated to electrically isolate the prong members 12, 14 from each other. As illustrated, bridge member 16 may be constructed from the same highly resistive substrate material 18.

The conductive coating material can be virtually any biocompatible material having sufficient conductivity to conduct electrical current. The material should also be suitable for permanent coating or permanent application upon the highly resistive substrate material. Exemplary metals which may serve as a conductive coating include gold, silver and platinum. The conductive coating material 20 may also be formed from biocompatible, conductive polymers, examples of which are well known to those having ordinary skill in the art.

The highly resistive substrate material 18 from which the clip 10 can be constructed includes both metals and biocompatible polymers. One preferred example of highly resistive metal is tungsten. Other suitable highly resistive metals are well known to those having ordinary skill in the art. Examples of highly resistive polymers include teflons, nylons, and others well known in the art.

As noted, the conductive coating material 20 should be of sufficient conductivity to conduct electrical current. Preferably, the conductivity of the material should be in the range of $10^4$ to $10^6$ mho-cm$^{-1}$.

In addition, the highly resistive material which serves as the substrate material should be of such low conductivity that it electrically isolates prong members 12, 14 from each other. The conductivity of this material should be in the range of $10^{-25}$ to $10^{-9}$ mho-cm$^{-1}$.

In one embodiment, a surgical clip is manufactured from a highly resistive material, such as tungsten, teflon or nylon, which is biocompatible and able to be deformed. Thereafter, prong members 12, 14 are made electrically conductive by permanently coating thereon a conductive material of the type mentioned above. One skilled in the art will appreciate that a variety of techniques may be employed to permanently apply the conductive coating material to the highly resistive substrate of the clip. Such techniques include, but are not limited to, sputtering and electroplating. A sufficient portion of the resistive substrate material 18 of bridge 16 remains uncoated with a conductive material so as to electrically isolate prong members 12 and 14 from each other.

Upon deployment of the present bipolar surgical clip to tissue, one of the prong members (e.g., prong member 12) serves as an active electrode for conveying electrosurgical energy to adjacent tissue. The other prong member (e.g., prong member 14) serves as a return electrode and communicates through ground wire 26 with an electrosurgical generator 22. The use of such a bipolar electrosurgical clip is advantageous in that electrosurgical current administered to the body travels only a short distance between the active and ground electrodes, thereby decreasing any potential risk of injury to the patient.

In a further embodiment of the invention, the substrate material is made of a biocompatible polymer having properties such that it will soften and become pliable at temperatures in the range of those it will encounter upon delivery of electrosurgical energy (e.g., about 125° F. to 145° F.). The prongs 12, 14 are coated with a conductive material. However, upon delivery of electrical energy to the clip, heat resulting from the electrical energy will be transferred from the coating to the plastic substrate. The clip will thus soften and become pliable. When the clip is deployed by an applicating device, it will close and be deformed. Once the heat dissipates, the clip will harden, become less brittle, and will more easily maintain its shape in the closed position.

The conductive coating typically is applied to the substrate in layers which are quite thin, but which are able to conduct electricity. The coatings may be applied at a thickness of about 1 to 3 mils, and in some applications the coating may be less than 1 mil in thickness. An example of an application which may require a conductive coating thickness of less than 1 mil is where the coating is intended to conduct electricity and to conduct heat to the substrate to render the substrate more pliable.

It is understood that various modifications and additions may be made to the present invention without departing from the intended scope thereof.

What is claimed is:

1. A surgical clip for tissue closure, comprising
   a pair of opposed prong members each having a conductive surface over at least a portion of the prongs for contact of tissue adjacent thereto;
   a bridge member joining the two prong members, the bridge member being constructed of a highly resistive material and serving to electrically isolate the prong members from each other, the bridge member and prong members being of a unitary construction.

2. The surgical clip of claim 1 wherein the bridge member and the prong members are formed of a highly resistive material, and at least a portion of each prong member is coated with a conductive material.

3. The surgical clip of claim 2 wherein at least a portion of the bridge member is coated with a conductive material, leaving a highly resistive portion of the bridge of suitable area to ensure electrical isolation of the prong members.

4. The surgical clip of claim 2 wherein the highly resistive material is a highly resistive metal having a conductivity in the range of $10^{-25}$ to $10^{-9}$ mho-cm$^{-1}$.

5. The surgical clip of claim 4 wherein the highly resistive metal is tungsten.

6. The surgical clip of claim 2 wherein the highly resistive material is a deformable, biocompatible polymer having a conductivity in the range of $10^{-25}$ to $10^{-9}$ mho-cm$^{-1}$.

7. The surgical clip of claim 6 wherein the biocompatible polymer is selected from the group consisting of teflons and nylons.

8. The surgical clip of claim 6 wherein the highly resistive material is a plastic substrate material having a softening temperature between about 125° to 145° F.

9. The surgical clip of claim 8 wherein the conductivity and coating thickness of the conductive coating are of dimensions which enable heat generated by applied electrical current to be transferred to the plastic substrate material through the conductive coating, the heat being in the range of about 125° to 145° F. and being sufficient to soften and render pliable the plastic substrate.

10. The surgical clip of claim 2 wherein the conductive material has a conductivity in the range of $10^4$ to $10^6$ mho-cm$^{-1}$.

11. The surgical clip of claim 10 where the conductive material is selected from the group consisting of gold, silver and platinum.

* * * * *